United States Patent [19]

Springston

[11] Patent Number: 4,966,785

[45] Date of Patent: Oct. 30, 1990

[54] METHOD FOR MAKING A NON-EXTRACTABLE STATIONARY PHASE OF POLYMER WITHIN A CAPILLARY COLUMN

[75] Inventor: Stephen R. Springston, Middle Island, N.Y.

[73] Assignee: Associated Universities, Inc., Washington, D.C.

[21] Appl. No.: 374,984

[22] Filed: Jul. 3, 1989

[51] Int. Cl.$^5$ .................... B01D 53/00; B05D 3/02; B05D 3/06

[52] U.S. Cl. .................................. 427/39; 427/41; 427/230; 427/238; 427/389.7; 427/221; 55/386

[58] Field of Search .............. 427/38, 39, 41, 230, 427/237, 221, 238, 389.7; 55/386

[56] References Cited

U.S. PATENT DOCUMENTS 4,376,641  3/1983  Nestrick et al. .................. 55/386
4,692,347  9/1987  Yasuda ............................. 427/41

OTHER PUBLICATIONS

Vossen et al., *Thin Film Processes*, (Academic Press, N.Y.), c. 1978, pp. 361–381.

Masada et al., *J. Of High Resolution Chromatography*, vol. 2, Jul. 1979, pp. 400–404.

*Primary Examiner*—Norman Morgenstern
*Assistant Examiner*—Margaret Bueker
*Attorney, Agent, or Firm*—Vale P. Myles

[57] ABSTRACT

A method for coating interior capillary column surfaces, or packing material of a packed column, used for gas chromatography, with a stationary polymer phase that is cross-linked by exposing it to a low-temperature plasma that is uniformly distributed over the column or packing material for a predetermined period of time to effect the desired degree of cross-linking of the coating.

10 Claims, 3 Drawing Sheets

METHOD FOR MAKING A NON-EXTRACTABLE STATIONARY PHASE OF POLYMER WITHIN A CAPILLARY COLUMN

This invention was made with Government support under contract number DE-AC02-76CH00016, between the U.S. Department of Energy and Associated Universities, Inc. The Government has certain rights in the invention.

BACKGROUND OF THE INVENTION

It has become common practice in recent years for chromatographers to form cross-linked polymer stationary phases within capillary columns in order to improve the performance of capillary gas chromatography within the columns. Because splitless and on-column injection techniques both flood the initial length of a column with solvent, which is sometimes at elevated temperatures, an untreated column will suffer progressive phase loss and resultant diminished efficiency due to rearrangement of the stationary-phase film. Alternatively, a properly cross-linked capillary column can be subjected to repeated solvent exposure without affecting its solute retention characteristics.

A further benefit arising from the insolubility of cross-linked polymer phases in such columns is the freedom to wash the columns with solvent for the purpose of removing non-volatile sample components. If these compounds fail to elute during a normal analysis, background noise can increase and interactions may occur with other sample components during subsequent analyses. The ability of cross-linked phases to resist dissolution has also facilitated the development of capillary supercritical fluid chromatography and open-tubular liquid chromatography with partition retention mechanisms.

Yet another advantage of cross-linking polymer coatings within such columns is to enhance the film stability. The relationship of the stationary-phase surface tension to the free surface energy of the columns substrate determines whether film disruption is thermodynamically favored. The kinetics of droplet formation however are greatly influenced by polymer viscosity. Thus, polar polysiloxane phases, which are normally subject to film disruption at elevated temperatures due to reductions in phase viscosity, will have enhanced physical stability when cross-linked.

There are known in the prior art a variety of techniques for cross-linking polymer phases in chromatographic columns. Siloxane polymers have received the most attention in this regard, but other phase classes have also been successfully cross-linked. Two distinctly different types of cross-linking can be considered for such applications, i.e., those with linkages formed either through the linear backbone of the polymer, or those with the linkages formed through substituent groups.

It is also known that in situ concatenation of a partially polymerized siloxane results in highly stable chromatographic column coatings. Cross-linked phases have been successfully prepared by adding tri- or tetra-functional silanes during the polymerization step to form the desired cross-linked phases. However, a major disadvantage of both of those known approaches is that they invariably suffer from increased stationary-phase activity due to the presence of uncapped functional sites on the silicon atoms.

A major improvement over such earlier known techniques was the application of free radical induced cross-linking to gas chromatography stationary phases. That approach, which was directly adapted from basic silicone chemistry developed in the 1950's, created cross-linkages through substituent groups, while leaving the polymer backbone intact. Because polymers that are not based on the siloxanes can have the same substituents, free radical cross-linking has also been applied to a broader range of stationary phases including polyethylene glycols. An advantage of this method is that it can be performed in situ after the phase has been deposited on a column wall.

Free radical cross-linking involves a chain reaction that is stimulated by a free radical initiator. Several different initiators have been successfully used. Earlier experiments were with organic peroxides, which decomposed upon heating to yield free radicals. The incorporation of active by-products into the stationary-phase layer was a problem with organic peroxides, as evidenced by adsorption of polar solutes. A second drawback was the elevated temperatures required to cause free radical formation. When heated, those phases exhibiting only marginal physical stability may coalesce into droplets, thus drastically reducing the operating efficiency of the column.

With each of the various chemical cross-linking agents, the incorporation of residual groups into the polymer structure can cause residual activity. A further drawback is that chemical initiators, except for ozone, which reacts spontaneously at room temperature, must be heated before cross-linking occurs. Even though the temperatures used to stimulate cross-linking are usually well below those encountered during separations, it may be preferable to avoid heating some polar phases before their mechanical stability has been augmented by cross-linking.

It has also been reported that free radicals can be formed directly in a stationary phase by irradiation with gamma rays. However columns prepared in this manner still exhibit undesirable adsorption of polar solutes. Other problems with irradiative cross-linking include damage to the outer polyimide coating and the general inaccessibility of suitable facilities for accomplishing such irradiation.

OBJECTS OF THE INVENTION

A primary object of the invention is to provide a method for readily and inexpensively preparing the inside surface of a capillary column that is to be used for gas chromatography and is to be coated with a stationary phase of cross-linked polymer that is relatively non-extractable.

Another object of the invention is to provide a method for cross-linking a polymer coating within a capillary column by a means that does not degrade column performance as measured by selectivity and efficiency.

Yet another object of the invention is to provide a method for cross-linking a polymer coating within a column in a manner such that adsorptive activity is not increased by the cross-linking procedure.

A still further objective of the invention is to provide a method for cross-linking stationary phases, which method is applicable across a broad spectrum of such stationary phases.

Yet another objective of the invention is to provide a method for successfully cross-linking high polarity polysiloxanes within a chromatographic column.

SUMMARY OF THE INVENTION

In a preferred arrangement of the present invention a method is provided for coating the inside surface of a capillary column with a stationary phase that is cross-linked in situ by exposing it to a low temperature plasma that is uniformly distributed over the coating to cross-link it and make it relatively non-extractable from the column. Such plasma-exposed polymers resist solvent dissolution. The preferred embodiment of the invention uses a simplified method for generating and uniformly distributing a low temperature plasma over a stationary phase coating within a capillary column. The invention is also useful in cross-linking stationary phase coatings on glass beads that are to be packed within a chromatographic column.

DESCRIPTION OF THE DRAWINGS

FIGS. 3 (a) and (b) are two chromatograms showing test solute peaks.

DESCRIPTION OF THE PREFERRED EMBODIMENT

Figure 1:
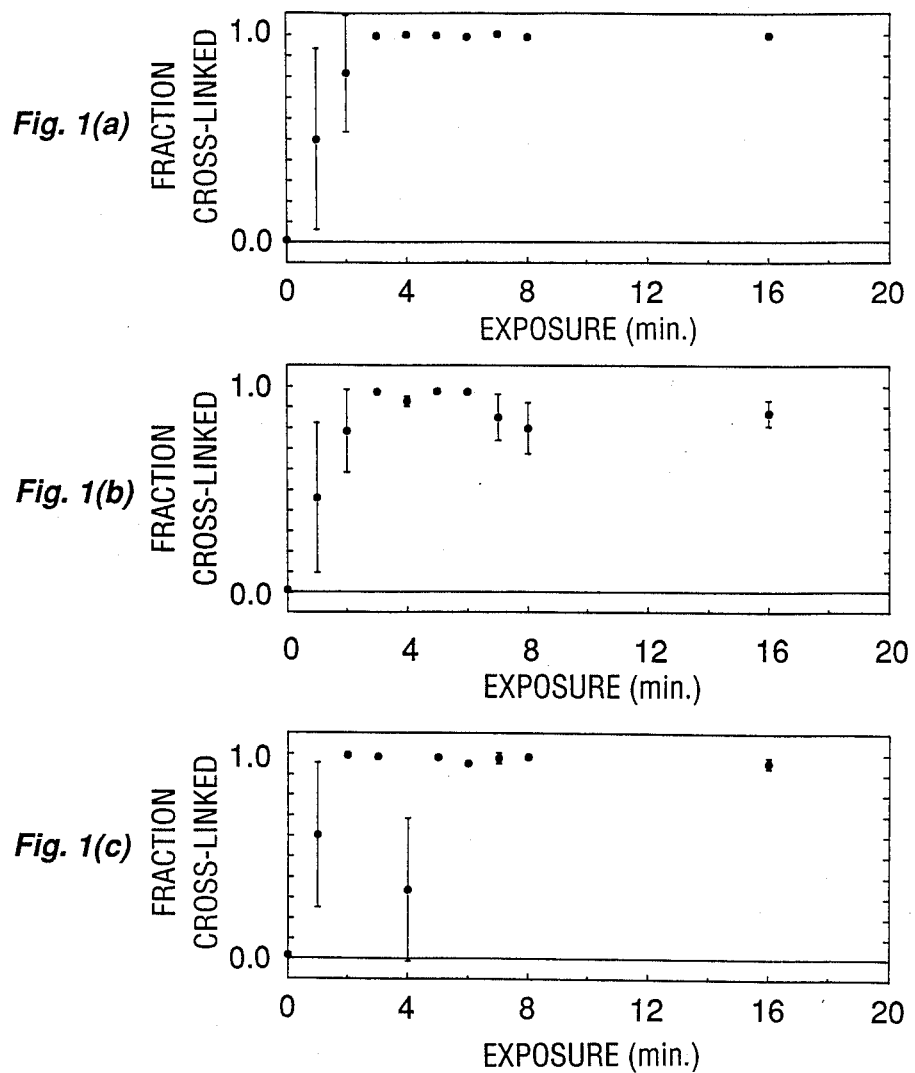
FIGS. 1 (a), (b) and (c) are three graphs showing the average fraction of a stationary polymer phase that remains on a glass surface after extraction, plotted vs. time of plasma exposure, for three different pressures of argon in the plasmas.

The present invention is a new method for achieving cross-linking of a stationary-phase polymer coating in a gas chromatography column, by applying a low-temperature plasma in a generally uniform fashion over the surface of the stationary phase. As used herein, a low-temperature plasma means a plasma that has an average electron energy between one and ten electron-volts (eV), and electron densities between $10^9$ and $10^{12}$ per cubic cm ($cm^{-3}$). The electrons in such plasmas are not in thermal equilibrium with the neutral species, with the gas temperature typically one or two orders of magnitude less than the electron temperature. Accordingly, while the gas remains near ambient temperature, energetic electrons stimulate chemical reactions by transferring energy to gas molecules and forming ions, free radicals, metastables and atoms. Those chemically active species then react with the polymer coatings in their vicinity to cause cross-linking of the polymer.

The method of the present invention has several advantages in cross-linking polymers for chromatographic purposes. First, low-temperature plasma are generated by the method of the invention in a controlled, low-pressure atmosphere, therefore, contamination of the column from extraneous species is minimized. Secondly, noble gases that are used as the plasma sustaining medium in the method of the invention, are not likely to become incorporated within the resultant cross-linked polymer coatings. Instead, those gases serve to initiate the free radical cross-linking chain reactions. Because the nobel gas atoms can be repeatedly energized in the plasma, free radicals are created as long as external energy is supplied to maintain the glow discharge or plasma. Furthermore, the method of the invention is made flexible for given applications because optimum values for gas pressure, composition, plasma excitation energy, and exposure time are all readily adjustable if necessary to accommodate different stationary phase polymers. Another important advantage of the method of the invention is that it permits plasma cross-linking of polymers by the use of external energy that is selectively coupled with gaseous plasma species, thereby avoiding indiscriminant application of heating throughout the entire column. Thus, direct heating of marginally stable stationary-phase films is minimized.

Although it is known that others have shown scanning electron micrographs of glass capillaries that were etched with plasmas of organo-fluorine compounds, and have also claimed to have plasma polymerized dimethyldichlorosilane on a column wall, it is not known that any successful chromatograms were produced to demonstrate such results. In fact, such films are probably inferior to conventional polysiloxanes for separating organic solutes as studies of plasma-polymerized siloxane monomers have shown their resultant polymers to exhibit a marked inorganic character.

To practice the preferred method of the invention for coating the inside surface of a capillary column useful for gas chromatography with a stationary phase polymer that is made relatively non-extractable, one first provides a capillary column with a suitable selected stationary phase polymer coating on the inner surface of the column. Means are then provided for exposing the stationary phase coating to a substantially uniformly distributed, low temperature plasma or glow discharge, for a pre-determined period of time, which should be at least two seconds in duration. While thus exposing the coating to the cross-linking effect of the plasma, a pre-determined pressure is maintained on the plasma of at least 0.1 Torr of a suitable gas from the group consisting of argon, helium, xenon, neon, or other gas including, but not limited to air, nitrogen, or any of the above with roughly 1% of methane or other suitable dopants, to convert the stationary polymer plasma to a cross-linked form without appreciably diminishing the chromatographic operating efficiency of the column.

A suitable low-temperature plasma for practicing the method of the invention can be produced by a number of different techniques. However, in the preferred embodiment an ordinary Tesla coil leak detector, which is commercially available from Fisher Scientific Company of Pittsburgh, Pa., was found to generate a desired level of glow discharge or plasma in low-pressured glass chambers by delivering an electrical arc of 50 kv and about 0.5 MHz. Other somewhat less suitable methods for producing a low temperature plasma of the type required to practice the present invention would be to substitute for the Tesla-coil generator a suitable conventional microwave generator such as the Little Litton, Model No. 1146 Microwave generator available from Litton Systems, of Minneapolis, Minn. Alternatively, a conventional commercially available radio frequency generator from a Low Temperature Dry Asher, commercially available from Tracerlab Company of Richmond, Calif. may be used. Also, a commercially available audio frequency generator, such as one taken from a Leco Induction Furnace No. 537, of the type sold by Laboratory Equipment Company of St. Joseph, Mich. were found to produced electrical fields of a desired low temperature variety when applied to the low-pressure argon gas confined within a capillary column, according to the method of the invention. In the case of radio-frequency excitation, at about 13.56 MHz, both capacitive and inductive coupling to the plasma within the column were observed. In relatively large diameter capillary columns, it was found that a plasma could be developed by means of applying voltage from a 7500-V neon sign transformer which had its high voltage coil operatively connected to a pair of spaced tungsten electrodes sealed into the ends of a capillary column.

In evaluating test runs with prototype apparatus used in practicing the method of the invention, the ability to cross-link stationary phases for chromatographic separations was assessed for both packed columns and open-tubular capillary columns. Chromatographic evaluation was done using a Varian Vista 4600 GC, from Varian Instruments of Walnut Creek, Calif., which was equipped with an on-column injector for packed columns and a split injector for capillary columns. Detection was accomplished with a flame ionization detector. Volumetric flow rates through the packed columns were maintained at about 10-mL/min., as measured by a soap bubble flowmeter. Linear flow rates of helium carrier gas through the capillary columns were between 20 and 30 cm/sec. and were not optimized. When comparing columns before and after a plasma treatment according to the method of the invention, the flow rate was maintained constant. All columns were evaluated based on efficiency and retention. Capillary columns were also assessed by the selectivity and activity shown for polar solutes.

Chromatograms were digitally recorded using a CHROM-1 A/D board, which is commercially available from Metrabyte Company of Taunton, Mass., operating within a commercially available micro computer such as that available from PC's, Limited of Austin, Tex. The software used to control the data acquisition was the program LABTECH NOTEBOOK (from Laboratory Technologies Corporation, Wilmington, Mass.). For packed column separations, the sample size was roughly 500 nanograms (ng). For capillary column evaluations, detector sensitivity was set so that less than 1 ng of an alkane produced a full-scale response (of $8 \times 10^{-12}$ AFS). Detector output was captured at 10 points/sec. with a height resolution of roughly 2000 points for a full-scale response. Moment analysis of the digital data was accomplished with software written in Pascal (available from Borland International Corp. of Scotts Valley, Calif.).

FIGS. 1 (a), (b), (c) show the average fraction of stationary phase that remains on a tested cover slip after extraction is plotted vs. time of plasma exposure to a low-temperature plasma, according to the method of the invention, using three different pressures of argon gas. Those three different pressures are, respectively, for graph (a) 0.1 torr, for graph (b) 1 torr, and for graph (c) 5 torr. After three minute plasma exposure periods at any of three selected pressures, the stationary phase polymer is shown to be insoluble and is considered to be essentially completely cross-linked. Except for a small number of tested cover slips, well over 95% of the cross-linked polymer remained on the tested cover slips, even after extensive extraction. However in a few cases, pieces of highly crossed linked material were dislodged from the glass and were observed in the extraction vessel. The plots shown in FIG. 1 confirm that a polysiloxane stationary phase can be converted into an essentially non-extractable form by relatively brief exposure to a low-temperature plasma according to the method of the invention. These data also indicate that plasma pressure only marginally affects the cross-linking process. Homogeneous pressures on the order of 0.1 to 10 Torr are easily achieved in the plasma reaction chamber used according to the techniques of the present invention to treat cover slips and column packing materials.

In general, it was found that the degree of cross-linking of the stationary phase due to plasma exposure according to the method of the invention decreases with increasing phenol substitution. SE-30, SE-52 and SE-54 (as obtained commercially from Alltech Associates of Deerfield, Ill.) all showed essentially complete cross-linking after exposure to a low temperature plasma for about 4 minutes, and more than 98% of the cross-linked phase resisted extraction. The more polar polysiloxanes remain partially soluble even after 16 minutes of exposure to the low-temperature plasma but they display evidence of some cross-linking. A 16-minute plasma exposure treatment resulted in about 20% cross-linking for OV-61 and roughly 10% cross-linking for OV-17 and OV-25 (obtained from Alltech Associates). All phases tested could be quantitatively extracted if they had not been subjected to plasma exposure according to the method of the invention. It should be understood that the SE materials referred to herein are commercially available from the General Electric Co., and the OV materials are produced commercially by Ohio Valley Co.

It has been reported that phenyl substitution hinders chemically induced cross-linking of polymers. Thus, the similar trend shown for the plasma-exposed cross-linking resulting from the inventor's tests of the present invention is consistent with the hypothesis that free radicals formed in the plasma initiate stationary-phase cross-linking. Of course, other factors, such as polymer chain length, polymer purity, and surface wetability, are likely to contribute to the observed differences in cross-linking for different phases and may obscure important distinctions between the two techniques.

Figure 2:
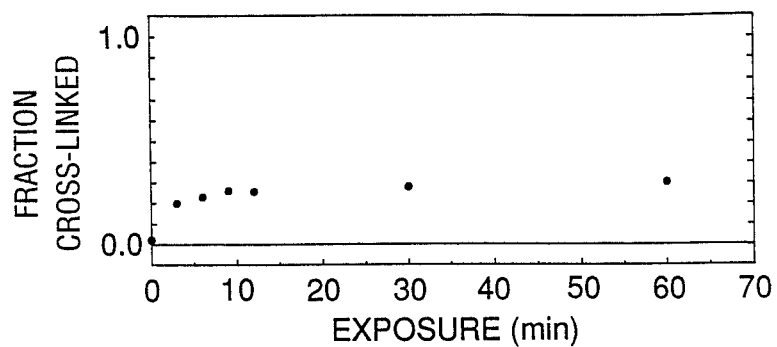
FIG. 2 is a graph that shows the fraction of a stationary polymer phase remaining on packing material that has been cross-linked and then extracted, as a function of exposure time to an extracting solvent.

FIG. 2 shows the fraction of cross-linked stationary phase polymer remaining on extracted packing material, as a function of its exposure time to a plasma, according to the method of the invention. Both the weight of polymer phase found in the extraction solvent and the weight loss measured for the packing material gave equivalent values of cross-linking. After exposure to a low-temperature plasma for about 6 minutes, the polymer stationary phase was 23% cross-linked. This value was not found to increase significantly even after repeated extended exposures of the polymer to the plasma, interspersed with mixing the glass beads upon which the polymer was coated. From these data it is concluded that reactive plasma components penetrate the inter-particulate spaces. However, though the plasma apparently penetrates between particles, the phase was not completely cross-linked even after prolonged exposure to the plasma.

In order to ascertain the chromatographic effects of the plasma caused cross-linking, tests were run using both cross-linked and non-cross-linked polymer coated packed columns for separating alkenes. At 100° C., the control column generated 2400 effective plates for decane at k′=22.5. Under identical conditions, a column packed with plasma treated cross-linked polymer coating material produced 2200 effective plates at k′=22.2. Sample retention was unchanged, confirming that the plasma exposure does not significantly alter solute solubility.

Due to the inability to completely cross-link the stationary phase polymers on ordinary packing, experiments with glass beads were performed using the method of the invention. With no internal pores available, the stationary phase polymer was confined to the surface of the beads. Low liquid phase loadings and reduced surface areas allowed the film thickness of capillary columns to be approximated in the experiments with the glass beads. An advantage of using such coated glass beads is that they can be removed from a column, extracted with solvent, and repacked in the column without damage. This flexibility allows the fraction of polymer that is cross-linked to be assessed either chromatographically or gravimetrically, when evaluating the method of the invention in this manner.

Of the various methods tested for generating a plasma in a capillary to practice the present invention, the use of a conventional Tesla coil was found to provide the most reliable low-temperature plasma. Two approaches for coupling the coil voltage to a capillary column were found to be useful. In the first approach a column containing argon gas at about 1 Torr was held centered in a 2 cm, inside diameter, glass tube, which was wrapped with ten turns of bare copper wire. The wire was touched to a terminal of the Tesla coil to cause a plasma to ignite over about a 20 cm length within the capillary column. The column was than pulled through this bright discharge in the outer tube at a rate of approximately 20 cm/sec. so that the entire column was briefly exposed to the plasma. However, it was observed that the polymer phase in columns cross-linked by this approach displayed relatively poor chromatographic performance, although they were complete resistant to solvent extraction. It is possible that the intense plasma developed by this approach causes damage to the polymeric stationary phase.

A second, more preferable approach, for producing the desired plasma for practicing the method of the invention is simpler, in that it was found to produce a much less vigorous plasma over the entire column. In this preferred approach, the Tesla coil is energized and brought closed to a metal cage that supports a capillary column containing argon gas at about 1 Torr pressure. As the tip of the coil approaches the metal cage, a faint glow discharge becomes visible throughout the entire column. This discharge flickers somewhat and appears as a pale greenish-orange, when viewed through the polyimide coating layer on the inside surface of the column. When the glow discharge is sustained for longer than 10 mins., the polyimide was found to degrade slightly at the points where it touches the metal cage. However, shorter exposure to the low temperature plasma had no apparent undesirable affect on the outer polyimide coating, as evidenced by undiminished column flexibility.

Figure 4:
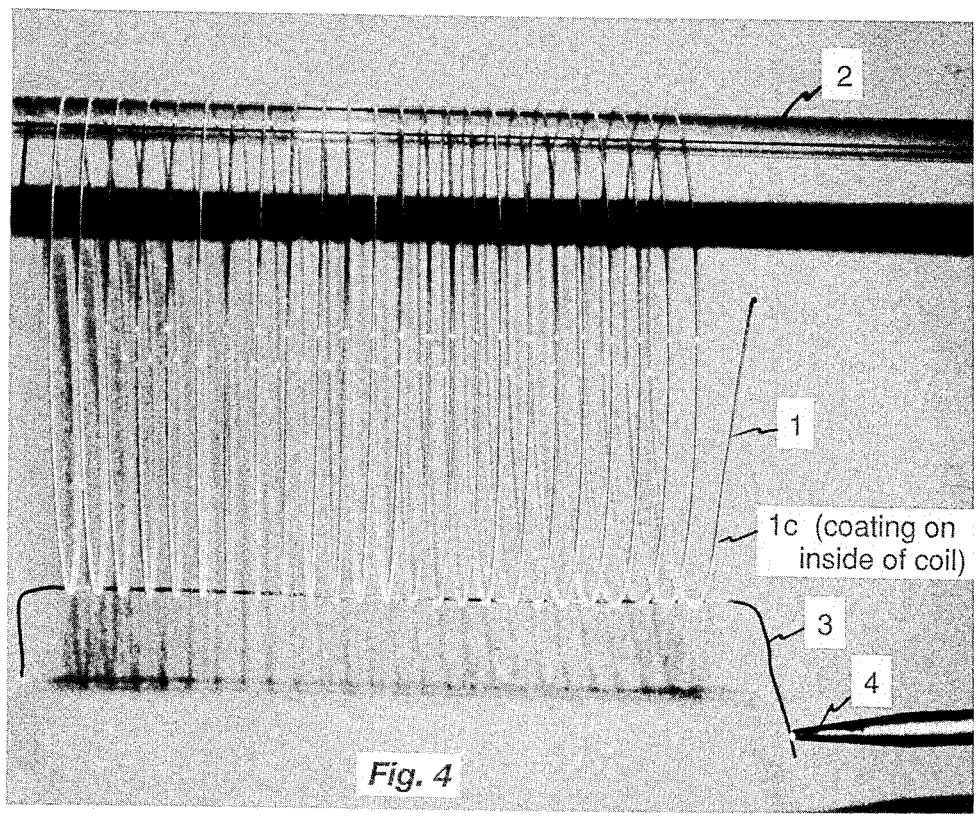
FIG. 4 is a side view photograph of a helically coiled capillary column, in combination with an electrically conductive wire that makes multiple spaced contacts with the coiled column. The column is supported on a glass rod and the wire is electrically connected to an output terminal of a Tesla coil (not shown), for practicing the method of the invention to establish a plasma shown in the column.

There is illustrated in FIG. 4 such an apparatus for practicing the method of the invention. A helically coiled capillary column 1 is supported, as shown, on a glass rod 2, or other suitable insulated support means. An electrically conductive wire 3 is positioned within the coil to contact it at a plurality of spaced points, as shown. One end of the wire 3 is electrically connected or touched with a tip 4 of a conventional Tesla coil generator (not further shown). The coil 3 is filled with argon, or other gas, as described above, and a generally uniform plasma is produced within the coil, originating at the points of contact between the coil and conductor 3. The light area at the bottom of the coil depict the plasma, thus formed. It should be understood that the capillary coil may be made of either glass or quartz and will typically be about 1 millimeter in outside diameter and about 0.25 mm in inside diameter. A conventional polymide coating 1c is applied to the inside of coil 1, before it is exposed to the plasma. The wire 3 acts as a metal cage in this embodiment, but it will be understood that quartz columns typically are commercially available in a form such that the coil is supported at multiple spaced points by a metal cage that may have a variety of different configurations.

To prepare a capillary column for use in practicing the method of the invention, the column should be extensively purged with argon or another suitable noble gas prior to its evacuation, thereby to minimize contamination by air within the column. It was also found that severe pressure gradients cause dramatic changes in plasma intensity over the column length, thus such variations should be minimized, even though the test data indicate that pressure gradients within a more moderate range should not interfere significantly with in situ cross-linking of capillary columns.

Table 2, below, shows data that demonstrates successful cross-linking of a polydimethysiloxane stationary phase within a capillary column.

TABLE 2

| Capillary Column No. | Stationary Phase | U.T.E. (%) | Fraction X-Linked (%) |
|---|---|---|---|
| 1 a | 0.4-w/v % SE-30 | 82 | — |
| c | | 39 | 23 |
| 2 a | 0.4-w/v % SE-30 | 87 +/−4 | — |
| b | | 37 +/−3 | — |
| c | | 40 +/−1 | 96 +/−3 |
| 3 a | 0.6-w/v % OV-215 | 72 | — |
| b | | 67 | — |
| c | | 31 | 36 |
| 4 a | 0.4-w/v % SuperOx 0.1 | 68 | — |
| b | | 38 | — |
| c | | 32 | 12 |

Utilization of Theoretical Efficiency (U.T.E.) is reported in Table 2 relative to an ideal column of the same diameter, providing identical solutes and retention at optimal flow velocity. The U.T.E. values shown here are conservative. Both detector and injector volume contribute slightly to band broadening as evidenced by a 5 to 10% increase in U.T.E. for 10-meter capillary columns. Capillary Column No. 1 is an untreated control. The dramatic loss in retention following extraction confirms that the phase is largely soluble. Greater pressure was required to force the polymer laden extraction solvent through this column than through the cross-linked columns. A second solvent wash of 10-mL removed an additional 3% of the original phase. The decrease in U.T.E. following extraction is largely due to the decrease in retention. The data for capillary column No. 2 are the average from three columns cross-linked independently. Solute retention was diminished only slightly by cross-linking with the method of the present invention. This minor reduction probably arose from conditioning before testing rather than from the plasma exposure. Solute retention was completely maintained after solvent extraction. A second solvent wash of 10-mL did not measurably alter retention, thus, these data confirm that plasma exposure with the method of the invention effectively cross-links the stationary phase polymer in such columns.

Figure 3A:
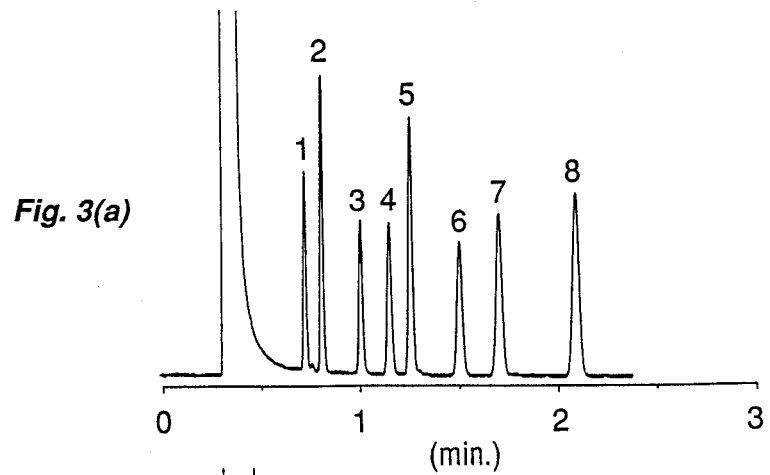
FIG. 3(a) is from a coated column before cross-linking.
Figure 3B:
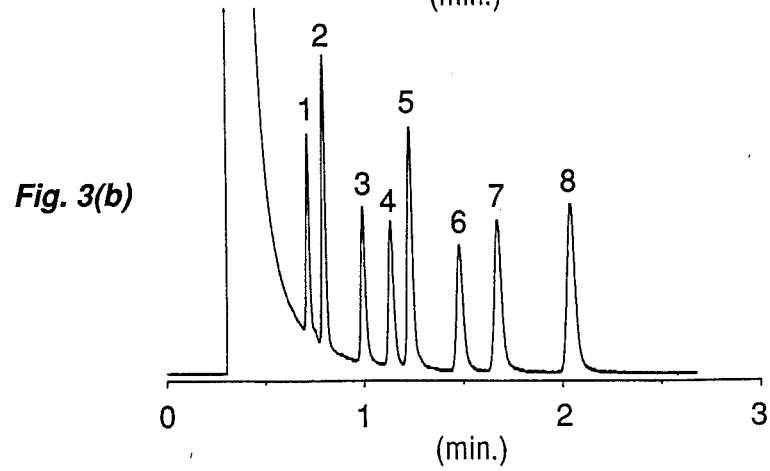
FIG. 3(b) was taken from the same column after cross-linking and exhaustive solvent extraction.

FIGS. 3 (a) and (b) illustrate chromatograms that indicate that the method of the invention somewhat reduces column efficiency. As shown in FIG. 3 (b), the test solute peaks all tail appreciably, with severe tailing in the solvent peak. The second statistical moment, used here to measure column efficiency, is highly sensitive to tailing peaks. This sensitivity is reflected in the low U.T.E. values for the cross-linked capillaries. It was found that plasma exposure of the stationary phase polymers does not change the peak areas for polar compounds relative to the alkanes. For properly diactivated columns, even the highly polar test solutes were found to elute with the proper peak area relative to the alkanes. Moreover, it was found that peak shape did not change significantly when the sample size was increased by a factor of 10, to 10-ng/compound on a tested column. These observations are not consistent with the usual cause of tailing, i.e. exposed active sites.

It was further found in practicing the method of the invention that inductively generated plasmas did not diminish exposed column efficiency when either column packing or glass beads were thus treated. Even exposure times well in excess of those needed for cross-linking showed no deleterious effects on packed columns. In practicing the method of the present invention, using a metal cage to support a capillary column, and applying a plasma-producing voltage from a Tesla coil to the supporting cage, it is believed that multiple tiny arcs are formed where the metal cage contacts the columns. These arcs apparently penetrate the fused-silica of the column, and the thin polymer layer before reaching the plasma in the column interior. It is believed that the film is damaged by the arc only at these small, very localized areas of contact. The test results shown in Table II for capillary column No. 3, coated with trifluoropropyl substituted polysiloxane, was partially cross-linked in situ. Unlike the polydiminethylsiloxane column, plasma exposure by itself did not greatly affect column efficiency. Extraction with the coating solvent removed 64% of the phase. Tests with the extracted column showed reduced column efficiency although the peak shape remained symmetrical in this instance. The reasons why OV-215 behaved differently than the SE-30 are not clear.

From the foregoing description of the invention, it should be apparent to those skilled in the art that various modifications and improvements of it may be developed without departing from the scope of the invention. Thus, it is my intention to encompass within the scope of the following claims the true limits of the invention.

I claim:

1. A method of coating the inside surface of a capillary column used for gas chromatography with a cross-linked polymer stationary phase that is relatively non-extractable, comprising the steps;

a. providing a capillary column with a stationary phase polymer coating on the inside surface thereof,
   b. exposing said stationary phase coating to a substantially uniformly distributed, low temperature plasma for a predetermined period of time of at least one second, while maintaining a predetermined pressure of at least 0.1 Torr on a plasma-supporting gas selected from the group consisting of argon, helium, xenon, neon, air, nitrogen, or mixtures thereof with any suitable dopant, whereby the stationary polymer phase is converted to a cross-linked form without appreciably diminishing the chromatographic operating efficiency of the column.

2. A method as defined in claim 1 wherein said stationary phase comprises a polymer selected from the group consisting of polysiloxane, polyethylene glycol; and other polymers having substituents susceptible to free radical cross-linking.

3. A method as defined in claim 1 wherein said predetermined pressure is maintained in the range of about 0.1 to 10 Torr.

4. A method as defined in claim 3 wherein said rare gas is argon and said predetermined pressure is about 0.1 Torr.

5. A method as defined in claim 1 wherein said predetermined period is in the range of 2 seconds to 25 minutes.

6. A method as defined in claim 1 including the step of supporting said column on an electrically conductive cage so that the cage contacts the column at generally uniformly spaced points, and including means for applying an electrical voltage to said cage, thereby to develop said low temperature plasma within the column.

7. A method as defined in claim 6 wherein said plasma can be generated within the column for at least 10 minutes, while an Argon gas within the column is maintained at a pressure of about 1 Torr.

8. A method as defined in claim 7 wherein said means for applying an electric voltage comprises electrically connecting a terminal of an energized Tesla coil to said cage.

9. A method of establishing a cross-linked form of polymer coated material within a column comprising the steps of;

(a) providing a plurality of glass beads, each of which are coated with a polysiloxane stationary phase, within a packed column,
   (b) exposing said coating on the beads to a low temperature plasma for about 5 minutes while maintaining a pressure of about 1 Torr of argon around the beads, thereby to cross-link the stationary phase,
   (c) removing the coated beads from the column and washing the beads with a solvent,
   (d) reinstalling the beads into the column, whereby the fraction of polymer that is cross-linked can be assessed either chromatographically or gravimetrically.

10. A method as defined in claim 8 including the step of providing a metal cage for supporting said column, and supporting the column on said cage so that a plurality of points along the column touch the cage at generally uniformly space points, thereby to establish a uniformly distributed, low temperature plasma within the column when a voltage is applied to the cage from the Tesla coil.

* * * * *